United States Patent
Crompton

(10) Patent No.: US 8,702,634 B2
(45) Date of Patent: Apr. 22, 2014

(54) MODULAR UPPER EXTREMITY SUPPORT SYSTEM

(76) Inventor: Wiltse Parker Crompton, Tomball, TX (US)

( * ) Notice: Subject to any disclaimer, the term of this patent is extended or adjusted under 35 U.S.C. 154(b) by 0 days.

(21) Appl. No.: 13/486,653

(22) Filed: Jun. 1, 2012

(65) Prior Publication Data

US 2012/0310130 A1    Dec. 6, 2012

Related U.S. Application Data

(60) Provisional application No. 61/491,960, filed on Jun. 1, 2011.

(51) Int. Cl.
*A61F 5/00* (2006.01)

(52) U.S. Cl.
USPC .................. 602/21; 602/22; 602/64; 128/879

(58) Field of Classification Search
USPC .................. 602/5, 21–22, 64, 75, 62–63; 128/878–880; 2/16, 18–21, 159–161.2, 2/161.4–161.7, 162–163
See application file for complete search history.

(56) References Cited

U.S. PATENT DOCUMENTS

| | | | |
|---|---|---|---|
| 859,097 A | 7/1907 | Miller | |
| 2,108,236 A | 2/1938 | Scott | |
| 3,556,091 A | 1/1971 | Haig | |
| 3,888,482 A * | 6/1975 | Starrett et al. | 473/458 |
| 4,103,682 A | 8/1978 | Franzl | |
| 4,214,579 A | 7/1980 | Ford | |
| 4,287,609 A * | 9/1981 | Amadeo | 2/16 |
| 4,369,775 A | 1/1983 | Gamm | |
| 4,632,105 A | 12/1986 | Barlow | |
| 4,781,178 A | 11/1988 | Gordon | |
| 4,881,533 A | 11/1989 | Teurlings | |
| 5,014,689 A | 5/1991 | Meunchen et al. | |
| 5,356,371 A | 10/1994 | Hubbard | |
| 5,415,624 A | 5/1995 | Williams | |
| 5,453,064 A | 9/1995 | Williams, Jr. et al. | |
| D373,639 S | 9/1996 | McKie | |
| 5,592,694 A | 1/1997 | Yewer, Jr. | |
| 5,682,611 A | 11/1997 | Kline | |
| 5,697,103 A | 12/1997 | Wiggins | |
| 5,916,186 A | 6/1999 | Turto et al. | |
| 6,557,177 B2 | 5/2003 | Hochmuth | |
| 6,561,995 B1 | 5/2003 | Thibodo, Jr. | |
| 6,702,772 B1 | 3/2004 | Colditz | |
| 7,001,352 B2 | 2/2006 | Farrell et al. | |
| 7,135,006 B1 | 11/2006 | Weber et al. | |
| 7,314,459 B2 * | 1/2008 | Bennett | 602/20 |
| 7,537,577 B2 | 5/2009 | Phelan et al. | |
| 7,854,714 B1 | 12/2010 | Weber et al. | |
| 7,887,497 B2 | 2/2011 | Weber et al. | |

(Continued)

*Primary Examiner* — Patricia Bianco
*Assistant Examiner* — Kari Petrik
(74) *Attorney, Agent, or Firm* — IP Authority, LLC; Ramraj Soundararajan

(57) ABSTRACT

A Modular Upper Extremity Support System (MUESS) improves hand function by optimizing the balance of flexion and extension at the wrist and stabilizing thumb abduction. This is accomplished through a basic support unit of a forearm cuff, a wrist extensor strap, and a web spacer strap. Various components and inserts can be attached to the basic support unit. The MUESS has several interchangeable components, inserts, and attachments, which allow the hand therapist and other caregivers to make adjustments to the orthotic in real time to support various hand functions that are critical to activities of daily living such as grasping.

19 Claims, 17 Drawing Sheets

(56) References Cited

U.S. PATENT DOCUMENTS

| | | |
|---|---|---|
| 7,914,475 B2 | 3/2011 | Wyatt et al. |
| 8,266,719 B2 * | 9/2012 | Duby .................. 2/161.1 |
| 2001/0046904 A1 | 11/2001 | Arvanitis, Jr. |
| 2003/0191421 A1 | 10/2003 | Weaver, II et al. |
| 2004/0049141 A1 | 3/2004 | Slautterback et al. |
| 2005/0197608 A1 | 9/2005 | Taylor et al. |
| 2006/0025711 A1 | 2/2006 | Bell et al. |
| 2006/0258965 A1 | 11/2006 | Lee et al. |
| 2011/0054371 A1 | 3/2011 | Colditz |

* cited by examiner

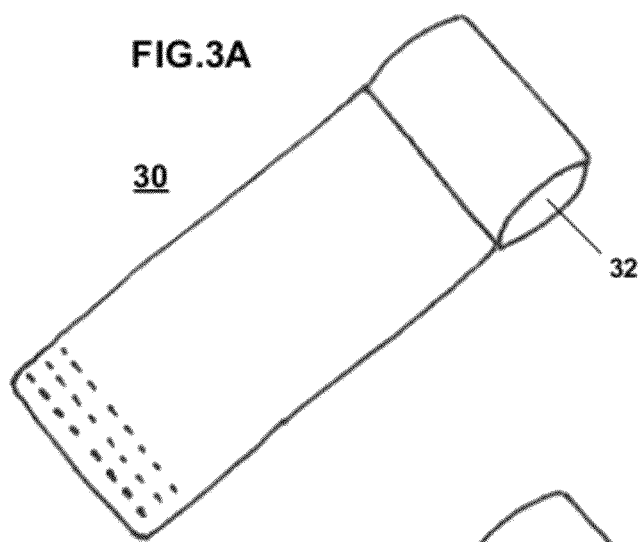
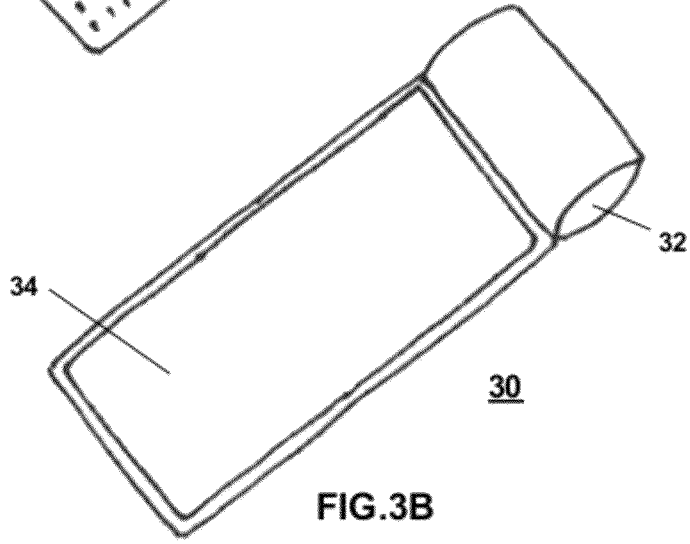

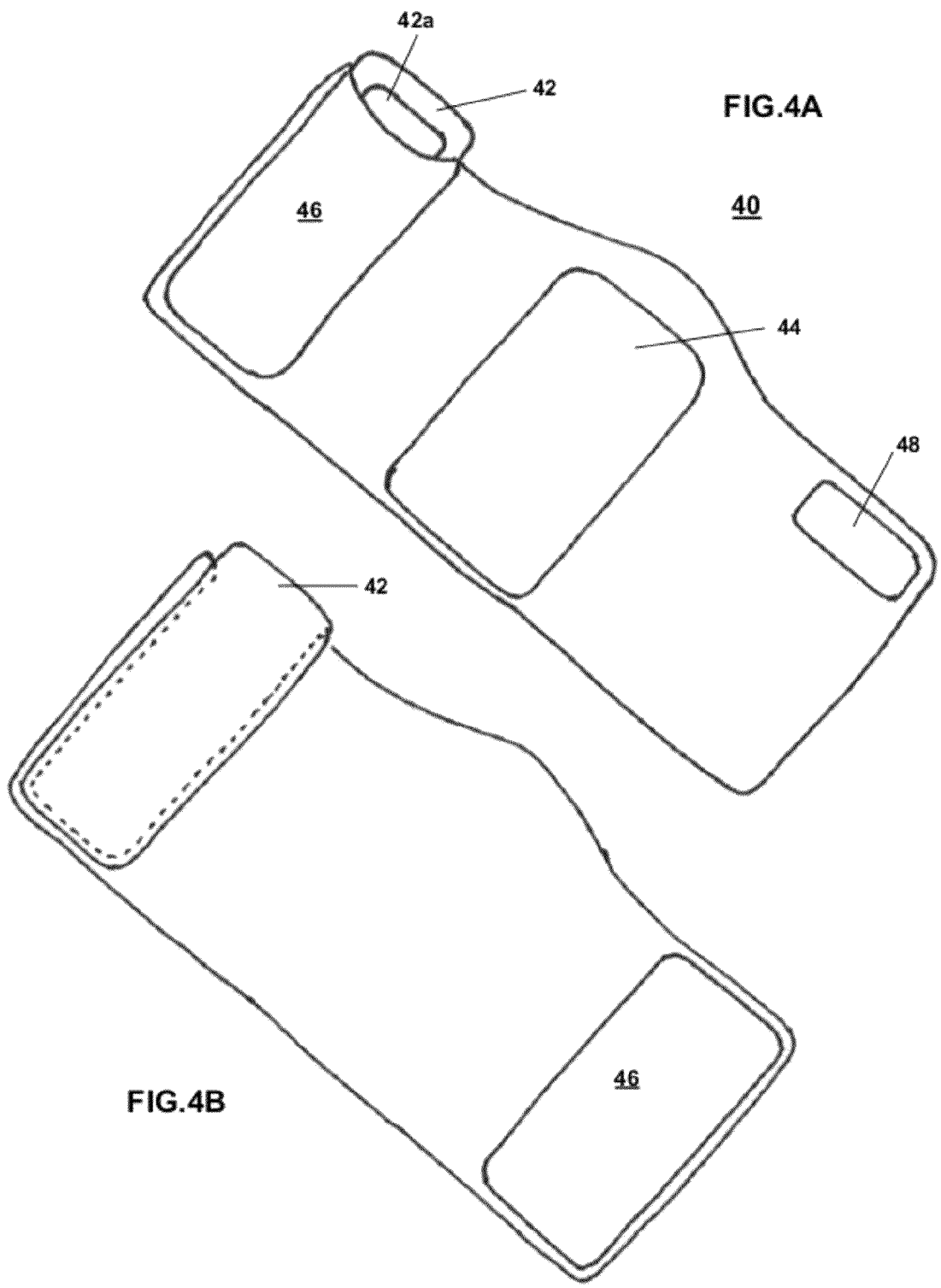

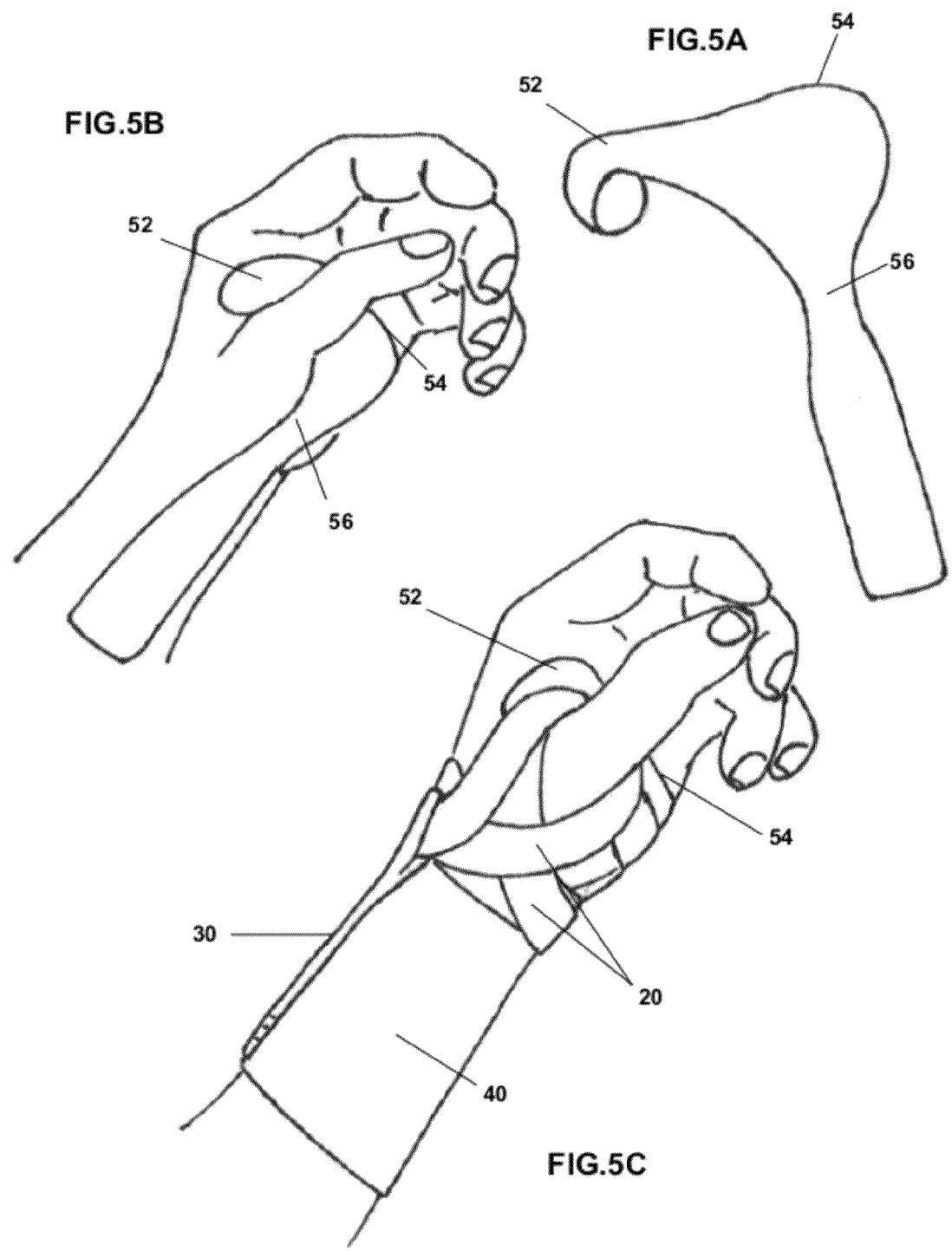

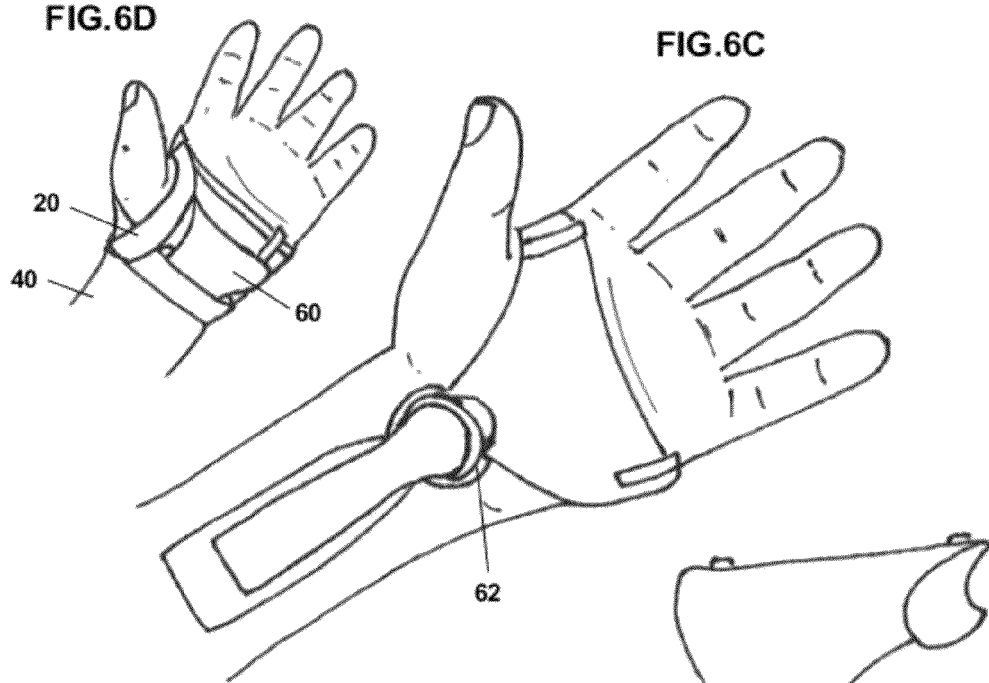
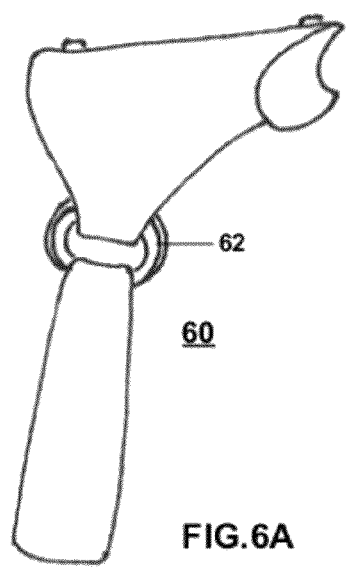
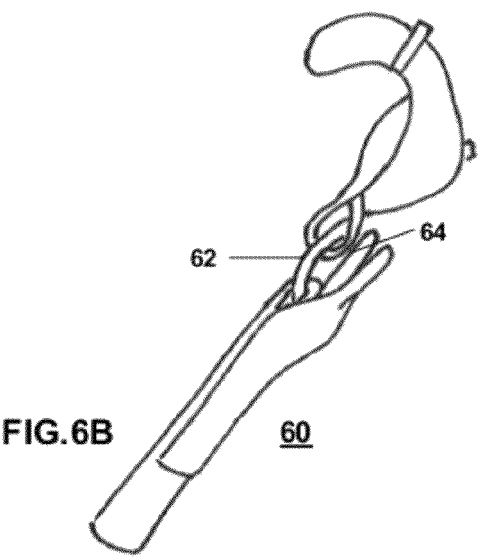

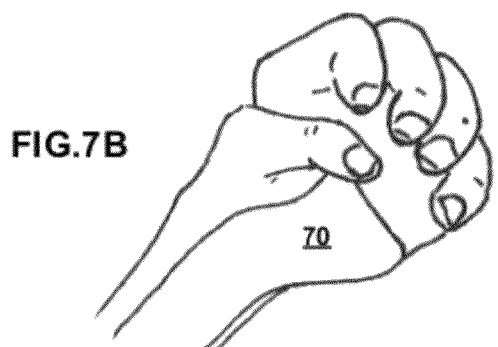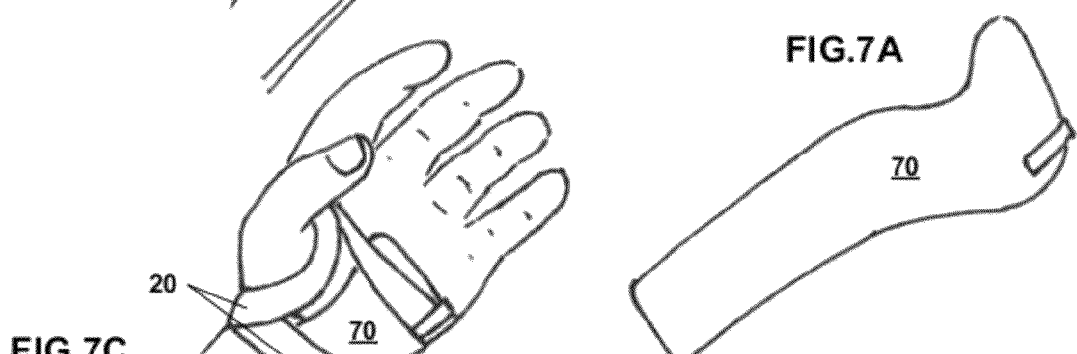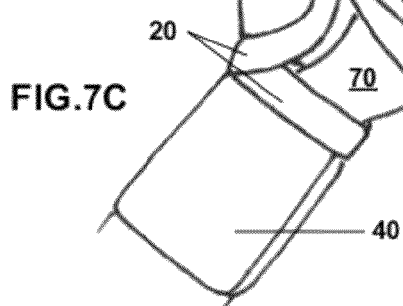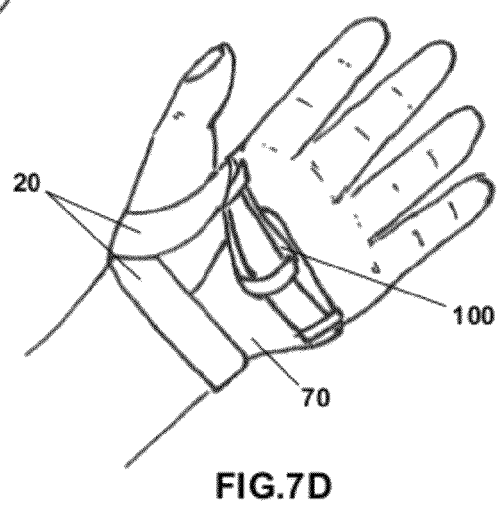

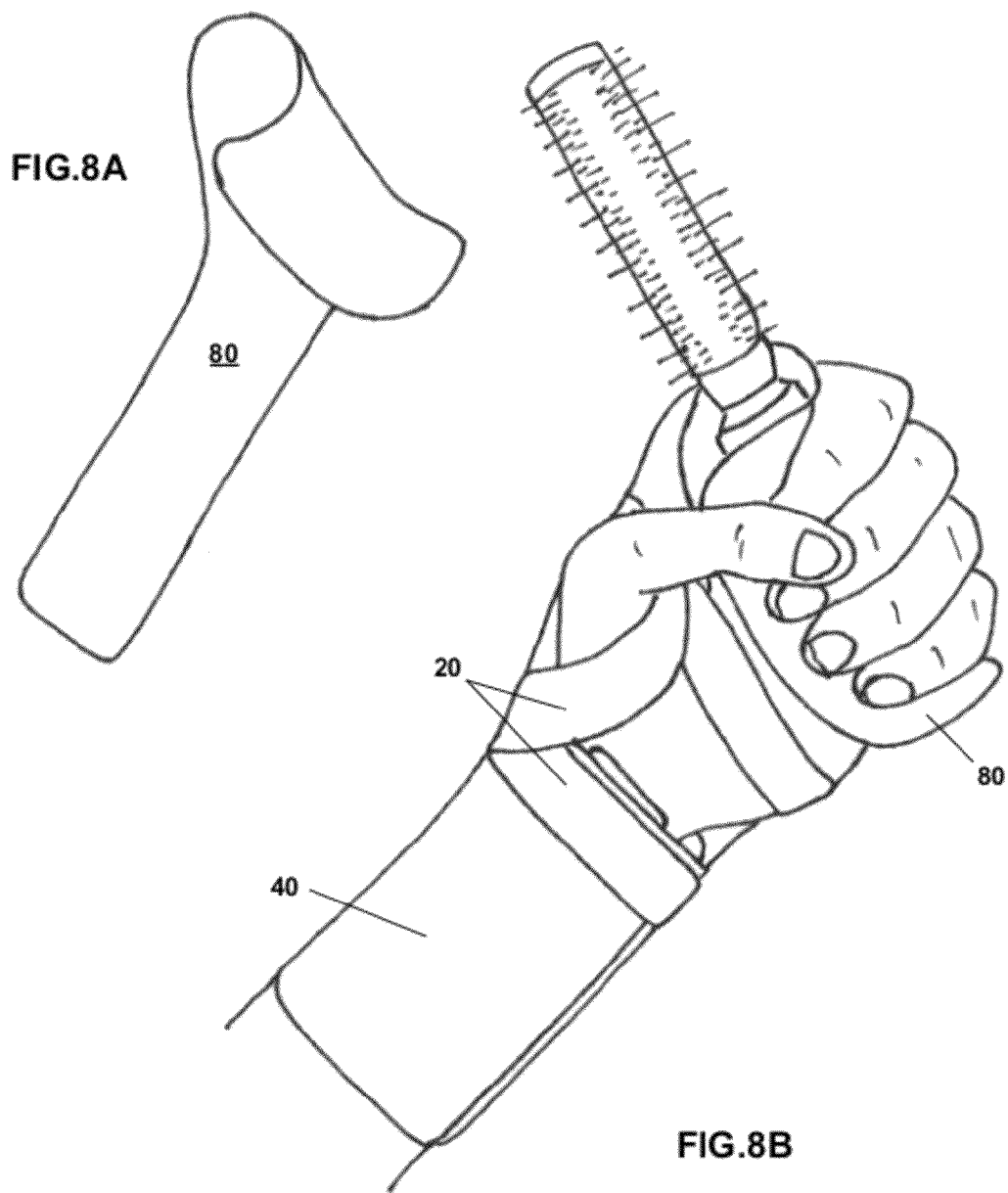

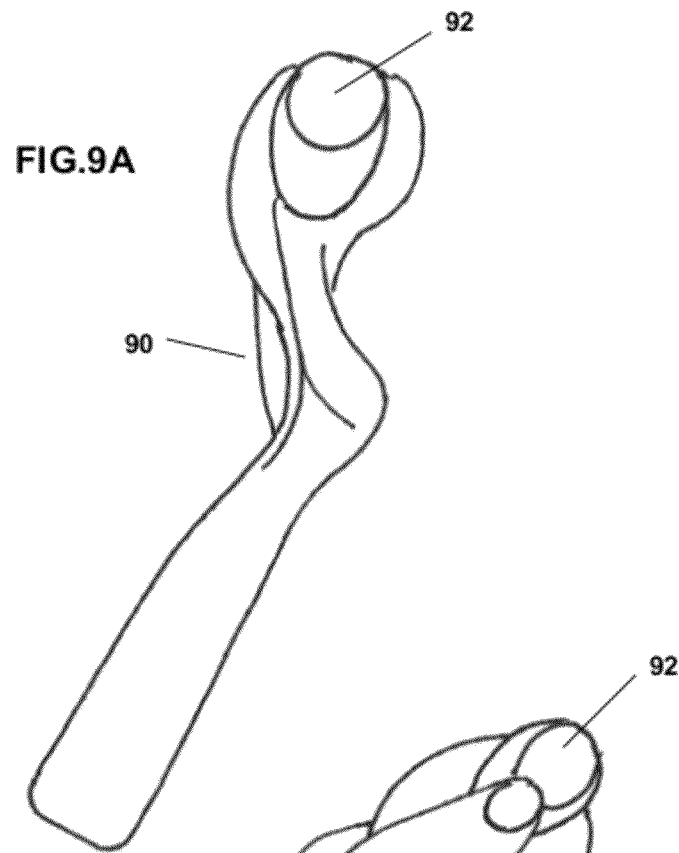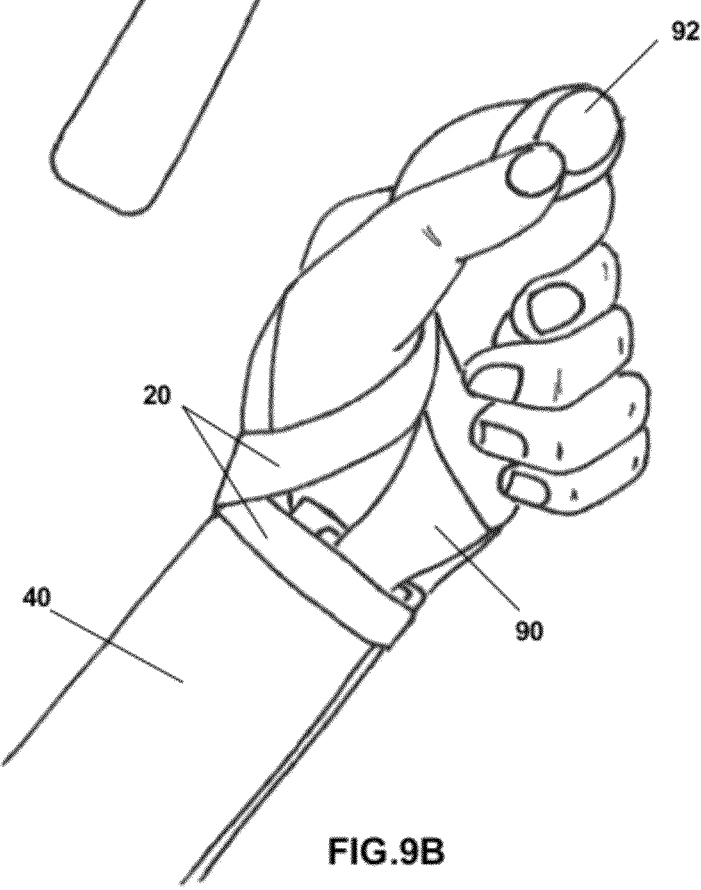

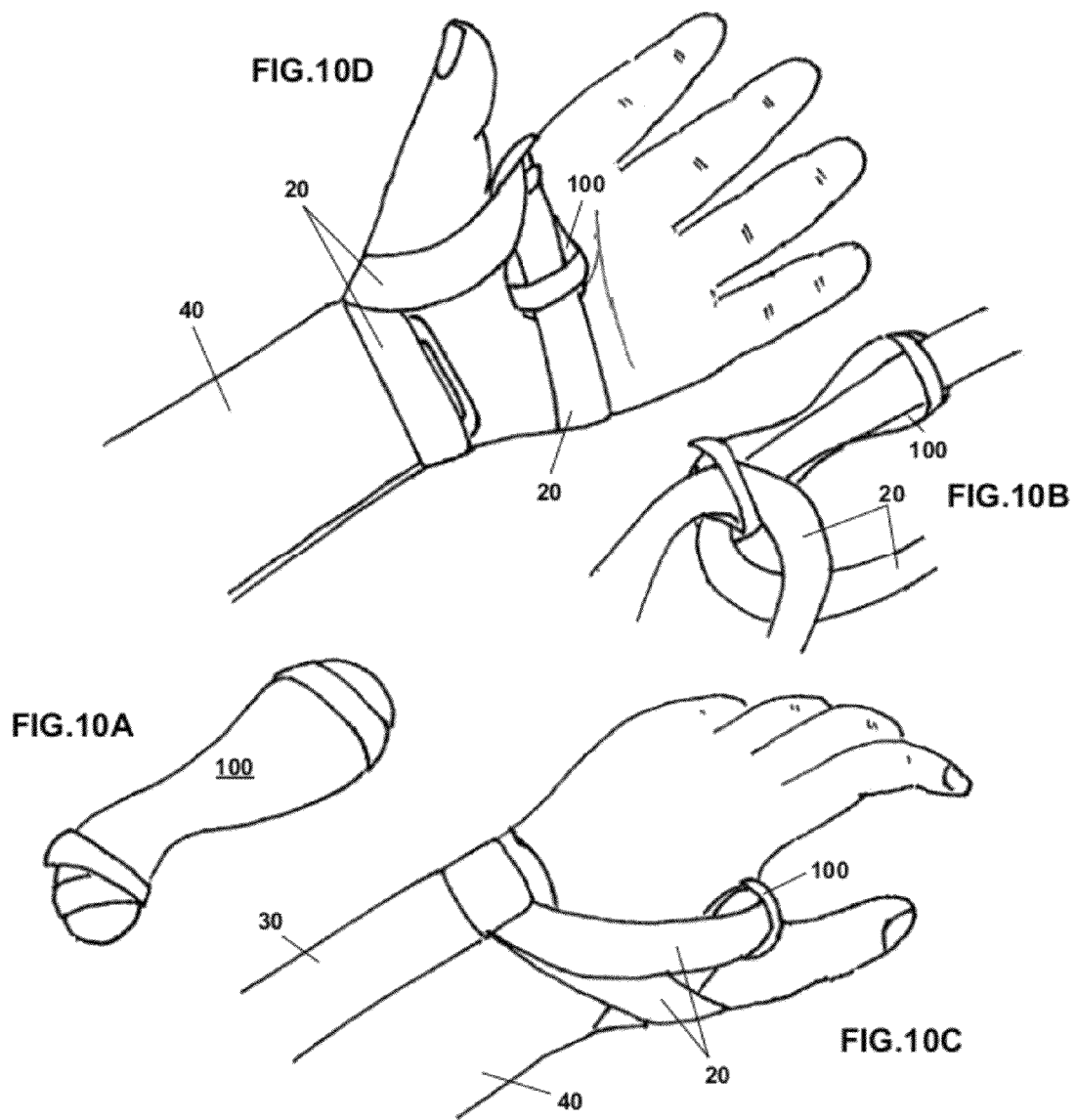

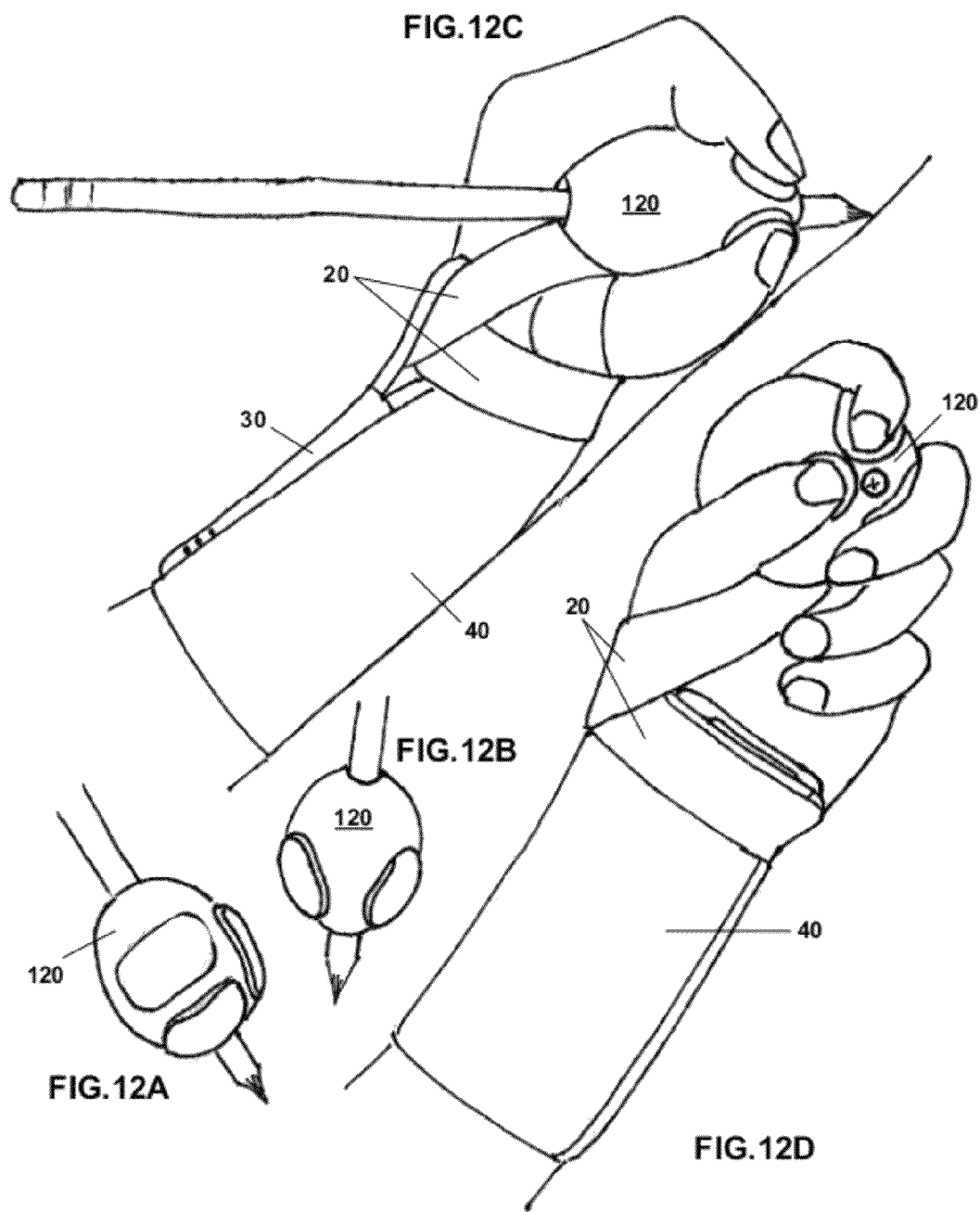

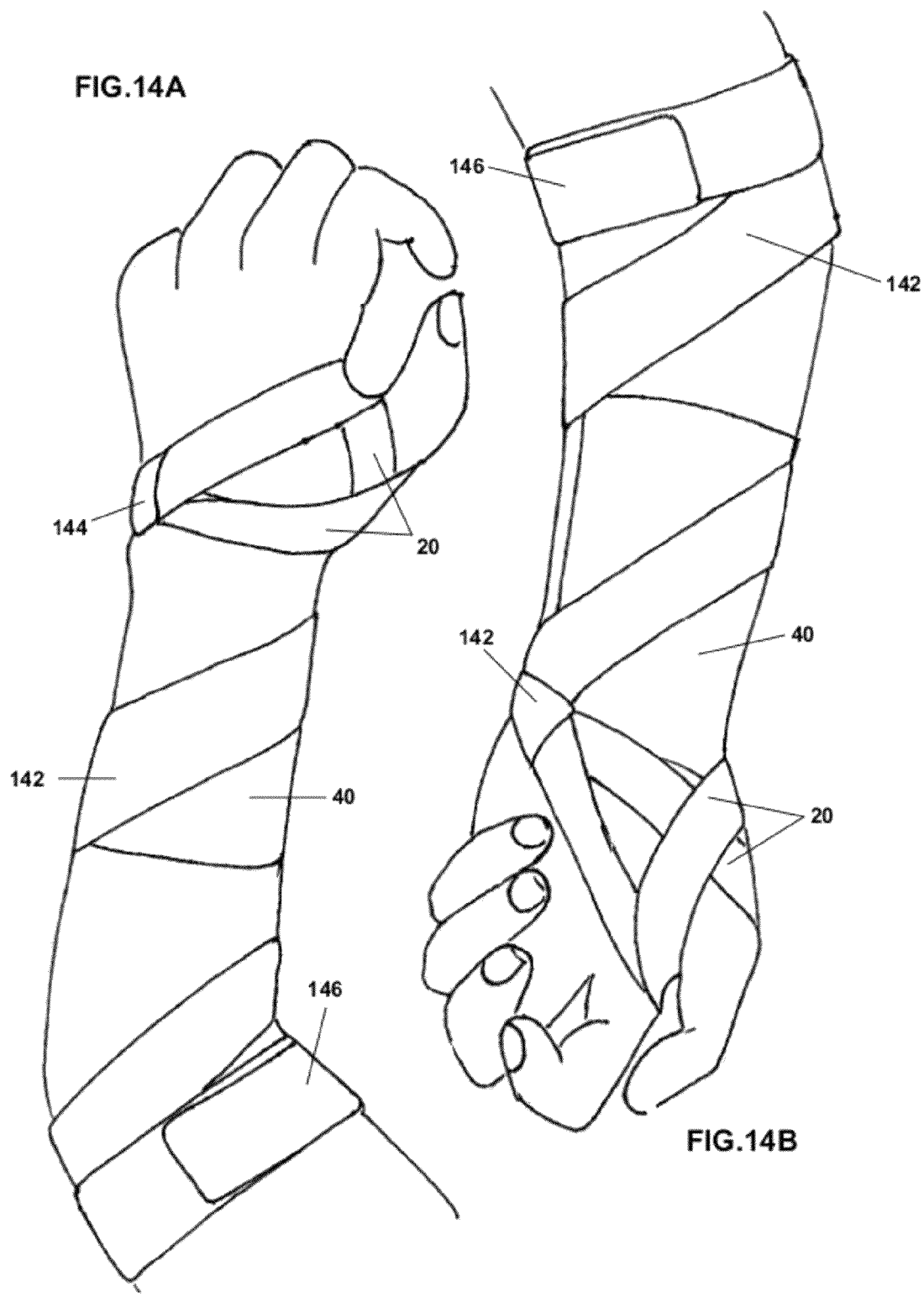

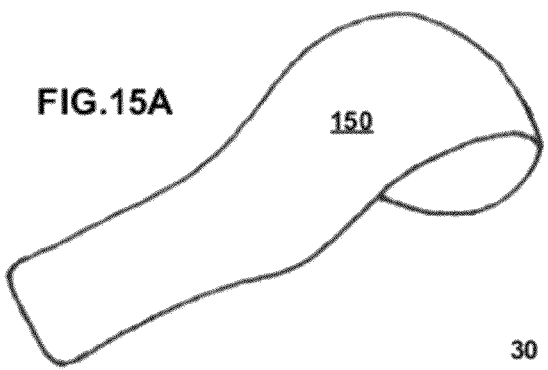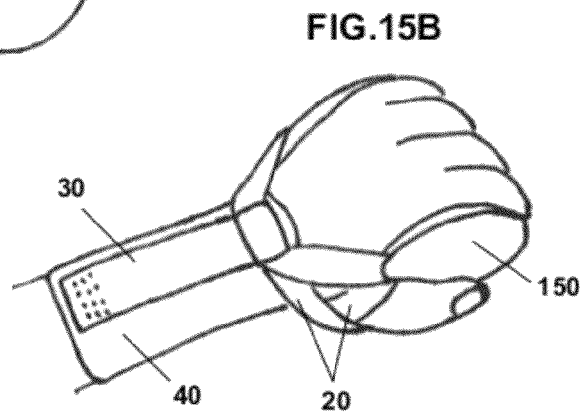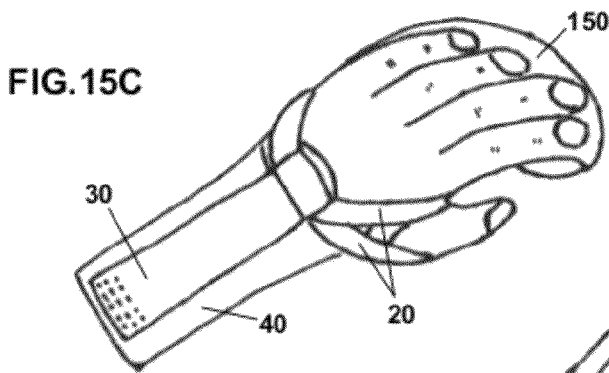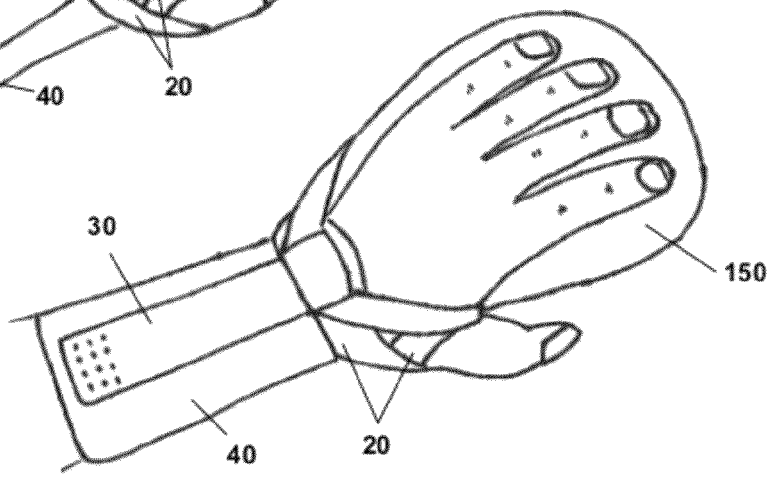

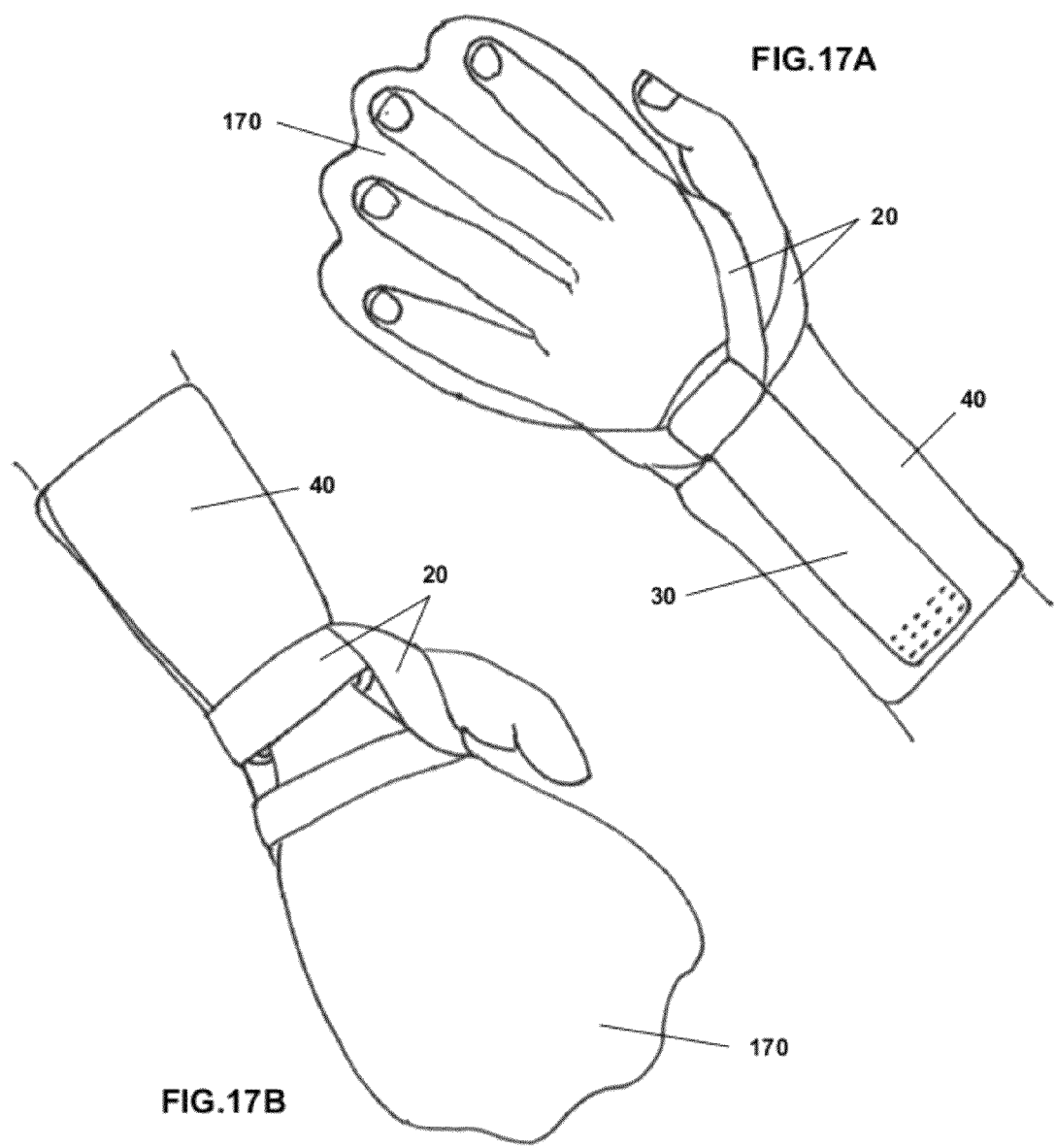

MODULAR UPPER EXTREMITY SUPPORT SYSTEM

RELATED APPLICATIONS

This application claims priority from U.S. Provisional Application Ser. No. 61/491,960 filed Jun. 1, 2011.

BACKGROUND OF THE INVENTION

1. Field of Invention

The present invention relates generally to the field of hand splints. More specifically, the present invention is related to flexible modular hand splints for use in treating hand dysfunction associated with central and/or peripheral nervous system injury.

2. Discussion of Prior Art

Experts in the management and treatment of hand dysfunction will recognize the therapeutic value of the Modular Upper Extremity Support System (MUESS) in treating hand dysfunction in children and adults with, but not limited to, the following diagnoses: cerebral palsy, cerebral vascular accident (stroke), traumatic brain injury, spinal cord injury, hydrocephalus, benign congenital hypotonia, dystonia, brachial plexus injury, and carpal tunnel syndrome; all of which involve an insult to the central, and/or peripheral nervous systems. However, for illustrative purposes, the present invention will be discussed in reference to hand dysfunction in children with cerebral palsy, a condition involving disruption of the complex organization and integration of the sensory and motor structures and pathways of both the central and peripheral nervous systems.

Children diagnosed with cerebral palsy (CP) experience decreased, increased, and/or fluctuating muscle tone which results in an imbalance of directional forces that manifest as stereotypical postures and movement patterns. For example, children with CP characteristically display hand and/or arm posturing with a reduced range of active motion which is typified by wrist and finger flexion, thumb adduction, ulnar deviation, and hand, wrist, and forearm pronation. These postures and movement patterns can result in contractures which further restrict movement and lead to mild to severe hand dysfunction.

The probability of improving hand function depends in part on the underlying cause and severity of the impairment, the services received, and the cognitive and visual status of the individual. However, even small improvements in hand function can be motivational and empowering, and contribute to increased independence in performing activities of daily living.

The development of hand skills follows a fairly predictable progression from infancy, through childhood and into the teen-age years. Those with expertise in the sensory-motor development of children are familiar with this pattern, and understand that neurological insults, whether experienced prenatally, neonatally or postnatally, may result in mild to severe disruption of this developmental pattern, ultimately leading to varying degrees of dysfunction and/or deformity. However, it is now widely accepted in the field of sensory-motor development that the plasticity of the nervous system offers the potential for improvement in sensory and motor function throughout life when appropriate therapy is implemented.

In the earliest stage of sensory-motor development, infants react automatically and reflexively by moving their arms and hands in response to tactile and proprioceptive somatosensory stimulation. As the nervous system matures, infants typically gain more control over reflexive responses, generally by six months of age. From that point forward, ongoing neurological maturation and environmental cues further promote hand skill development which progresses from voluntary motor patterns of grasp, release, and bi-manual skills in young children to refinement of fine motor skills during teen-age years and into adulthood.

However, infants and young children with cerebral palsy often have low proximal and distal muscle tone initially, followed later by high distal tone, the latter which often becomes apparent when they experience physical or emotional distress as might be experienced when attempting to move against gravity. Unable to counter the pull of gravity due to low proximal muscle tone, these children may try to stabilize with their extremities when making the effort to move away from a supporting surface, which in turn leads to high distal tone making it very difficult for them to hold their own weight and remain upright against gravity. The stress of the circumstance increases muscle tone in the extremities as the child pulls down to the supporting surface, making an attempt to stabilize in synergistic patterns of flexion and/or extension, often manifested with stereotypical posturing of the upper extremities into shoulder internal rotation, elbow extension, finger and wrist flexion, ulnar deviation, and pronation, further leading, over time, to contractures of the soft tissues.

Subsequently, the learned motor patterns of young children with neurological deficits may be dominated by reflexive behaviors which lack voluntary control and lead to dysfunctional grasping patterns that resemble those of infants of six months of age or younger, leaving them with severely restricted range of motion.

Individuals with neurologic injuries may have deficits in fine motor skills that range from mild impairments of hand function to more severe patterns that require orthotic support of the hand, wrist, and forearm. Often orthotics are designed to improve bone and joint alignment to prevent the development of contractures (tightening of soft tissues). Such orthotics, however, tend to be immobilizing which can further hinder the development of functional hand use.

Prior art modular wrist splint systems such as those described in U.S. Pat. Nos. 4,369,775 and 7,537,577, as well as US Patent Application Publication 2011/0054371 are overly restrictive and do not allow the flexibility in hand movements allowed by the MUESS while still providing the support needed for changing, functional requirements.

Whatever the precise merits, features, and advantages of the above cited references, none of them achieves or fulfills the purposes of the present invention.

The MUESS supports and positions the hand, wrist, and forearm to optimize and facilitate both passive and active movement resulting in improved hand function. In children with cerebral palsy, the imbalance of directional forces is most evident clinically at the wrist and thumb, which typically manifests as a synergistic pattern of wrist and finger flexion, thumb adduction, ulnar deviation, and forearm and hand pronation. Thus the focus of the invention is to first establish improved balance of flexion and extension at the wrist, along with thumb abduction which optimally positions the hand, wrist, and forearm for functional movement originating at the joints of the wrist and thumb. By increasing stability through improved alignment of the bones, the MUESS promotes functional mobility through the joints of the hand, wrist, and forearm. When integrated into other early intervention services, the MUESS system improves hand function in children with neurological injuries. The MUESS also increases tactile and proprioceptive somatosensory input through gentle compression of the hand, wrist, and forearm, which benefits individuals with nervous system deficits who may have significantly reduced opportunities to receive, experience, interpret and integrate sensory-motor information.

It is proposed that the present invention addresses, and reasonably meets, the aforementioned needs. The components of the Modular Upper Extremity Support System (MUESS) interact dynamically to provide combinations of stability and mobility which increase the potential for improved functional hand use and skill acquisition in individuals with central and/or peripheral nervous system disorders having mild to severe impairments in hand function.

SUMMARY OF THE INVENTION

A modular upper extremity support system (MUESS) basic unit with a forearm cuff surrounding an individual user's forearm, a wrist extensor strap attached to the forearm strap along the dorsal side of the user's forearm, and a web spacer strap with a loop at one end of the web spacer strap that wraps around the user's thumb proximal to the metacarpophalangeal joint before crossing the volar surface of the user's hand and another loop at the other end of the web spacer strap that wraps around the user's thumb proximal to the metacarpophalangeal joint after crossing the dorsal surface of the user's hand. The wrist extensor strap has a pocket at a distal end that captures and secures the web spacer strap.

The present invention also treats hand dysfunction in an individual user by wrapping a forearm cuff around the forearm of the user, looping a loop on one end of a web spacer strap around the user's thumb below the metacarpophalangeal joint, running the web spacer strap across the volar surface of the user's hand, running the web spacer strap around the ulnar side of the user's hand, running the web spacer strap across the dorsal side of the user's hand and through a pocket in the distal end of a wrist extensor strap, looping a second loop of said web spacer strap around the user's thumb below the metacarpophalangeal joint, and attaching a wrist extensor strap to the dorsal side of the forearm cuff.

Another embodiment of the present invention is a modular upper extremity support system (MUESS) with a forearm cuff with a plurality of support pockets of varying width located on the inside of the forearm cuff adjacent to the user's skin along the volar side of the user's forearm. The MUESS also has a wrist extensor strap attached to the forearm strap along the dorsal side of the user's forearm, and a web spacer strap with a loop at one end of the web spacer strap that wraps around the user's thumb proximal to the metacarpophalangeal joint before crossing the volar surface of the user's hand and another loop at the other end of the web spacer strap that wraps around the user's thumb proximal to the metacarpophalangeal joint after crossing the dorsal surface of the user's hand and passing through a pocket in the distal end of the wrist extensor strap that captures and secures the web spacer strap. The MUESS also includes at least one modular element in conjunction with the basic unit. The modular element may be a dynamic wrap-around, a mobile joint facilitator, a wrist/ulnar support, a toy/tool holder, a lateral pinch exerciser, a web space widener, an incremental web spacer, a graphomotor tool holder, a finger isolator, a hand/wrist/forearm rotator, a weight bearing wrap, a radial/ulnar finger positioner, or a resting hand support.

Another embodiment includes a forearm cuff that has at least one support pocket on the inside of said forearm cuff adjacent to the user's skin along the volar side of the user's forearm for holding an orthotic insert. The support pockets may be of varying width. The orthotic insert may be a dynamic wrap-around, a mobile joint facilitator, a wrist/ulnar support, a toy/tool holder, a lateral pinch exerciser, a weight bearing wrap, or a resting hand support. Still other embodiments include a modular attachment on the web spacer strap, such as a web space widener, an incremental web spacer, or a graphomotor tool holder. A further embodiment includes a modular attachment, such as a finger isolator, a hand/wrist/forearm rotator, or a radial/ulnar finger positioner.

Another embodiment includes web spacer strap with a sliding fastener that adjusts the circumference of the web spacer strap. The web spacer strap may additionally have a hook and loop fastener to attach a portion of the web spacer strap directly to the forearm cuff. One more embodiment includes a wrist extensor strap that is attached to the forearm cuff with a repositionable hook and loop fastener.

BRIEF DESCRIPTION OF THE DRAWINGS

FIGS. 3A and 3B illustrate a wrist extensor strap.
FIGS. 4A and 4B illustrate a forearm cuff.
FIGS. 5A-C illustrate a dynamic wrap-around element for use in the MUESS.
FIGS. 6A-D illustrate a mobile joint facilitator element for use in the MUESS.
FIGS. 7A-D illustrate a wrist/ulnar support element for use in the MUESS.
FIGS. 8A and 8B illustrate a toy/tool holder element for use in the MUESS.
FIGS. 9A and 9B illustrate a lateral pinch exerciser element for use in the MUESS.
FIGS. 10A-D illustrate a web space widener element for use in the MUESS.
FIGS. 12A-D illustrate a graphomotor tool holder element for use in the MUESS.
FIGS. 14A and 14B illustrate a hand/wrist/forearm rotator for use in the MUESS.
FIGS. 15A-D illustrate a weight bearing wrap element for use in the MUESS.
FIGS. 17A and 17B illustrate a resting hand support for use in the MUESS.

DESCRIPTION OF THE PREFERRED EMBODIMENTS

Figure 1A:
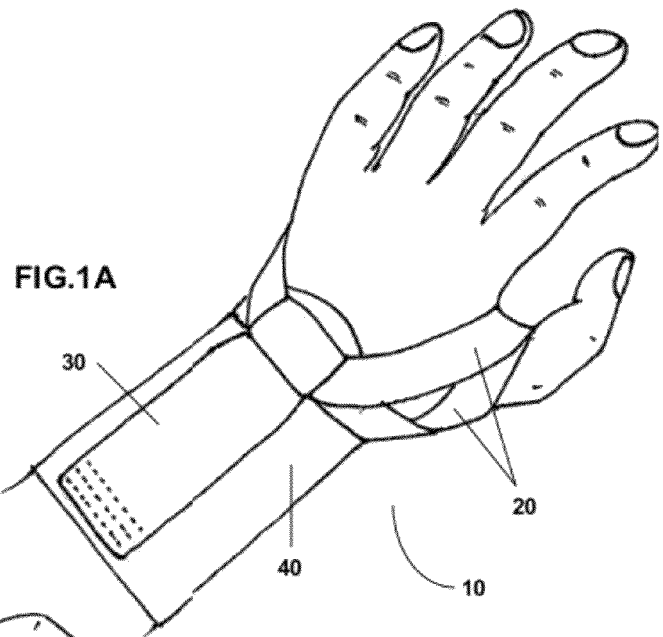
FIGS. 1A-C illustrate a basic unit of the Modular Upper Extremity Support System (MUESS).

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The MUESS is comprised of MUESS Basic Unit 10 and modular inserts and attachments, as will be described below. The MUESS Basic Unit 10, as shown in FIG. 1, includes the Wrist/Forearm Cuff 40 to which two connected, functionally related straps—the Web Spacer Strap 20 and the Wrist Extensor Strap 30—are attached. The modular inserts and attachments are secured in support pocket 42 on the Wrist/Forearm Cuff 40 or in the palm by the Web Spacer Strap 20, respectively. The interchangeable modular inserts and attachments can be combined and recombined to provide optimal support for the changing needs of the user, such as increasing active range of motion, assisting with self-care, engaging in play/recreational activities, and/or providing support for passive, static positioning.

There are at least two types of thermoplastic modular inserts which differ in thickness and width, and can be interchangeably inserted into a wider or narrower support pocket 42 on the Wrist/Forearm Cuff 40. This allows the rigidity/flexibility of the MUESS to be adjusted to accommodate varying degrees of hand, wrist, and forearm weakness and/or synergy spasticity among individuals.

The combined effect of the support offered by the MUESS assists in facilitating a more balanced interaction between the flexor and extensor muscles, thus increasing the potential for mobility, including rotation, of the hand, wrist, and forearm. The MUESS also prevents contracture formation and lessens the severity of already formed contractures.

The MUESS insert and attachment modules are interchangeable which allows the individual's doctor, orthotist, and/or therapist to provide customized facilitation of active movement, as well as passive positioning of the fingers, wrist, and hand according to the needs of the patient.

The MUESS is more functional, adaptable and less restrictive than other currently available hand orthoses, and so it is anticipated that compliance with its recommended use will be high.

Figure 1B:
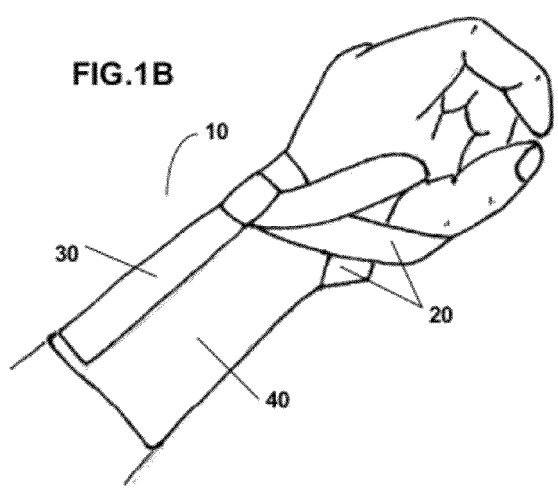
Figure 1C:
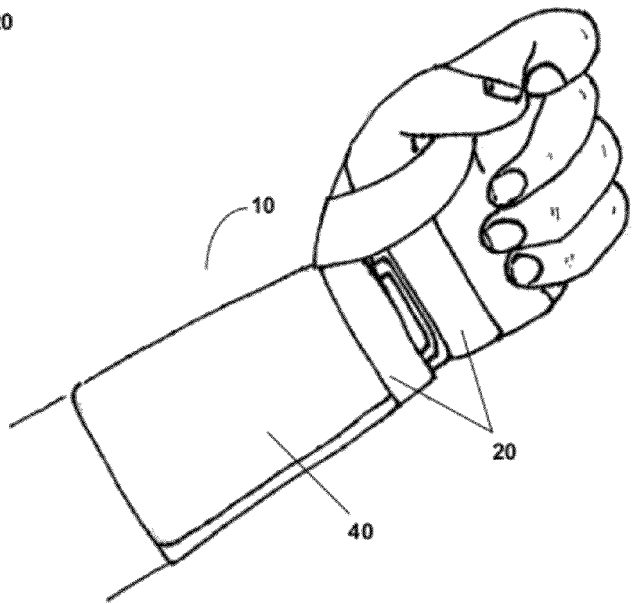

The MUESS Basic Unit 10 shown in FIGS. 1A-C is an orthotic constructed by encasing the Web Spacer Strap 40 in a pocket at the distal portion of the Wrist Extensor Strap 30, creating two loops which wrap around the thumb, alternately. The first loop is placed around the thumb prior to crossing the palm, and the second loop is placed around the thumb after crossing the back of the hand. The Wrist Extensor Strap 30 is then secured by a hook and loop fastener to the center of the dorsal surface of the Wrist/Forearm Cuff 40. Components of the MUESS Basic Unit 10 are made from, but not limited to, foam laminated between two layers of non-latex nylon.

Figure 2A:
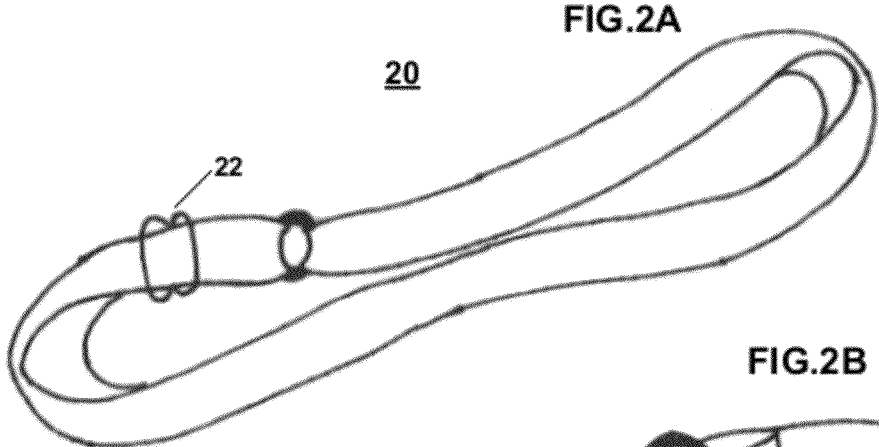
FIGS. 2A-C illustrate a web spacer strap.
Figure 2B:
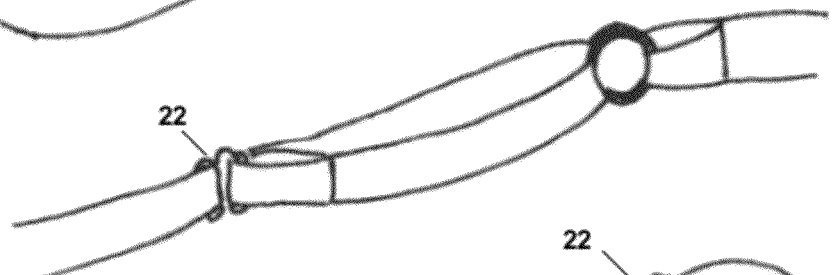
Figure 2C:
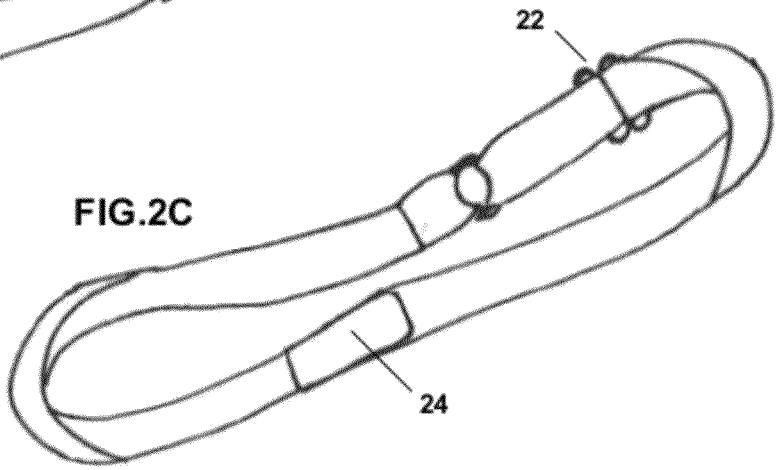

The Web Spacer Strap 20 shown in FIGS. 2A-C is attached at both ends by a fastener which slides to increase or decrease its circumference. FIG. 2B shows a close up view of the sliding fastener that is used to adjust Web Spacer Strap 20. The Web Spacer Strap 20 is encased in the pocket 32 at the distal end of the Wrist Extensor Strap 30, with the distal segment of the Web Spacer Strap 20 placed on top of the proximal segment, creating two loops, each of which is wrapped around the thumb in opposite directions. The Web Spacer Strap 20, in combination with the Wrist Extensor Strap 30 and the Wrist/Forearm Cuff 40, assist in bringing the thumb out of the palm, and passively placing the thumb in a position alongside the index finger, for potential opposition with the fingers, as well as passively placing the hand in slight wrist extension. The two segments of the Web Spacer Strap 20, which are on the dorsal surface of the hand and horizontally cross the four metacarpals of the fingers, are secured together in the pocket 32 of the distal portion of the Wrist Extensor Strap 30 with the distal segment lying on top of the proximal segment. The two segments of the Web Spacer Strap 20 on the volar surface of the hand remain separate, with the more distal segment crossing the palm at an approximate diagonal of the transverse arch, and the more proximal segment attached to the distal end of the Wrist/Forearm Cuff 40 by a hook and loop fastener. Both volar segments of the Web Spacer Strap 20 secure the thermoplastic and/or attachment modules. With the Web Spacer Strap 20 encased within the pocket 32 of the Wrist Extensor Strap 30, the latter is pulled proximally until the pocket 32 lies over the carpal bones of the wrist, a point mechanically serving as a fulcrum between the forearm and hand. The Web Spacer Strap 20 does not cover the metacarpophalangeal or interphalangeal thumb joints, and thus does not restrict movement of these joints. The Web Spacer Strap 20 is constructed from material of varying degrees of resistance to sufficiently counter the pull of flexor spasticity if present, and is securely attached at the two ends by a sliding fastener 22, which can be easily lengthened or shortened to allow for adjustments that achieve a comfortable, customized fit. The Web Spacer Strap 20 also includes hook and loop fastener 28 that can be used to secure a portion of Web Spacer Strap 20 directly to Wrist/Forearm Cuff 40.

The Web Spacer Strap 20 is donned by looping one end over the thumb with the palm facing up, bringing it across the dorsal surface of the hand, around the ulnar side, crossing the volar surface, and looping the other end around the thumb. The two loops cross just below the metacarpophalangeal joint, leaving the joint uncovered and unrestricted, whether passively positioned or actively in use. The first loop facilitates slight cupping of the hand, and the second loop opens the web space to assist in abduction of the thumb.

FIGS. 3A and 3B show the front and back, respectively of Wrist Extensor Strap 30 which connects the Web Spacer Strap 20 with the Wrist/Forearm Cuff 40 in a dynamic, interactive relationship, exerting a directional pull of the hand into extension at the wrist, and the thumb in position alongside the finger. By passively moving the thumb out of the palm, with the hand in position of slight wrist extension, with readiness for movement, the potential for improving functional grasping patterns is increased. Depending on the need to increase or decrease tension of the pull, due to dystonia, hypotonia, hypertonia, and/or fluctuating tone, Wrist Extensor Strap 30 can be adjusted by moving it along Wrist/Forearm Cuff 40, away from or towards the hand, respectively, by detaching and reattaching hook and loop fastener 34, thus changing degree of wrist extension and thumb adduction/abduction.

FIGS. 4A and 4B show the wrist/forearm cuff secured around wrist and forearm by a hook and loop fastener 46, providing a point of attachment 44 for combined unit of the Web Spacer Strap 20 and the Wrist Extensor Strap 30 on dorsal surface of Wrist/Forearm Cuff 40. On the volar surface of the Wrist/Forearm Cuff 40, which is in direct contact with the skin of the forearm, are a wide support pocket 42 and a narrow support pocket 42a, sewn over the hook portion of the hook and loop fastener 46 to hold a more rigid or more flexible modular insert, respectively. Inserted into one of the two support pockets 42 and 42a, is one of the following interchangeable modular inserts: Dynamic Wrap-Around 50, Mobile Joint Facilitator 60, Wrist/Ulnar Support 70, Toy/Tool Holder 80, Lateral Pinch Exerciser 90, Weight Bearing Wrap, or Resting Hand Support. On the volar surface of the Wrist/Forearm Cuff 40, the proximal portion of the Web Spacer Strap 20 attaches to the distal end of the Wrist/Forearm Cuff 40, by a hook and loop fastener 48. The circumference of the Wrist/Forearm Cuff 40 can be increased or decreased by adjusting the hook and loop closure 46 to the right or left.

Supplemental to the MUESS Basic Unit 10 are modular inserts and modular attachments which are used when the hand is pulled (by an increase of muscle tone, gravity, and/or contractures) into a synergistic pattern characterized by flexion of the fingers and wrist, adduction of the thumb, ulnar deviation of the wrist, and/or pronation of the forearm. Common to at least five modular inserts, including the Dynamic Wrap-Around 50, the Mobile Joint Facilitator 60, the Wrist/Ulnar Support 70, the Toy/Tool Holder 80, and the Lateral Pinch Exerciser 90, are the following characteristics:

- Increase the potential for functional hand use by positioning the hand in slight wrist extension and thumb abduction, in concurrence with the counterbalancing pull of the adjustable Web Spacer Strap 20 and Wrist Extensor Strap 30, against excessive flexion and/or ulnar deviation of the wrist.
- Counter the flexor pull of a severely spastic hand, wrist, and/or forearm by maintaining the position of the hand within a range of active movement of approximately 10 degrees of wrist extension to 20 degrees of wrist flexion, in which range an individual with a strong synergistic pattern of flexor spasticity can realistically be encouraged to develop functional grasping patterns.
- Resistance provided by the modular insert ranges from the least to most restrictive, as determined by the strength of the pull into a synergistic pattern of flexion, the latter also ranging from mild to severe.
- Either narrowed or widened, over the fulcrum of the wrist joint, where also either thinned or thickened, in both instances to the appropriate degree, as determined by the clinical reasoning of an orthotist and/or a therapist.
- Enable an individual to benefit from tenodesis, in which naturally occurring flexion of the wrist results in extension of the fingers and thumb, and extension of the wrist results in flexion of the fingers and thumb.
- Although with use of the modular inserts the active range of motion of the wrist of an individual with a severely spastic hand is restricted to within approximately 30 degrees, an improved functional pattern of grasp and release is obtainable.
- Constructed from, but not limited to, thermoplastic which is heated and molded to fit the contours of an individual's hand, wrist, and forearm, customizing each modular insert to allow for changing needs.
- Formed with slight concavity, mid-center over the palm, to provide gentle, tone inhibiting compression.
- Strength of the modular insert is varied by decreasing or increasing the thickness and/or the width of the thermoplastic, to provide minimal to maximum support of the hand, wrist, and forearm, respectively, as determined by the extent of the disability and the clinical reasoning of the orthotist and/or therapist.
- Flexibility or rigidity of the modular insert is achieved by decreasing or increasing the strength of the thermoplastic over carpal bones of the wrist, thus allowing more or less flexion, respectively, at the wrist joint.
- Used in combination with the MUESS Basic Unit 10.
- Interchangeable within a support pocket 42 or 42a of the Wrist/Forearm Cuff 40 as needed to enable and/or facilitate, varying activities of daily living.
- Proximal portion inserts into either the wide support pocket 42 or narrow support pocket 42a on the Wrist/Forearm Cuff 40 depending on whether the Modular Insert requires more or less strength, to counter the flexor pull of the hand of the individual wearer, respectively.
- Curve slightly away from skin of the individual wearer for comfort and to prevent skin chafing.
- Adhesive padding added on the undersurface to cushion contact with soft tissues and boney prominences as determined by the orthotist and/or therapist.

FIGS. 5A-C show further features of embodiments of the Dynamic Wrap-Around 50, which is a modular insert used in combination with the MUESS Basic Unit 10. The web spacer portion 52 of Dynamic Wrap-Around 50 narrows and thins as it curves away from the skin and passes over the web space between the thumb and index fingers. It places pressure on soft tissue only, and ends at dorsal surface of the hand between the metacarpals of the index finger and thumb, slightly proximal to their metacarpophalangeal joints. Soft material, such as gel foam, silicone, or moleskin, added on the undersurface or around web spacer portion cushions contact with metacarpals and metacarpophalengeal joints of thumb and index finger. The top border 54 of Dynamic Wrap-Around 50 lies slightly below transverse palmar arch, and allows approximately 80 degrees of flexion at metacarpophalangeal joints with which grasping and releasing using tenodesis may be achieved. The ulnar portion 56 of Dynamic Wrap-Around 50 has the border depth increased or decreased for more or less stability or mobility, respectively. It wraps around ulnar side of hand, and ends as it reaches the dorsal side of hand.

FIGS. 6A-D show features of the Mobile Joint Facilitator 60, which is a modular insert used in combination with the MUESS Basic Unit 10. The Mobile Joint Facilitator 60 comprises a moveable joint placed over volar surface of wrist, with a flexible ring 62 connecting the two thermoplastic portions covering the hand and forearm. The distal portion of Mobile Joint Facilitator 60 is placed over the flexible ring 62 of the moveable joint with a cushion of silicone 64 between the two for smoothness of rotational movement of the wrist. FIGS. 7A-D show features of the Wrist/Ulnar Support 70, which is an insert which is used in combination with the MUESS Basic Unit 10. Wrist/Ulnar Support 70 may be used in combination with Web Space Widener 100 for increased stability. FIGS. 8A and 8B show features of the Toy/Tool Holder 80, which is an insert used in combination with the MUESS Basic Unit 10 that holds an inserted object for functional and/or recreational use. FIGS. 9A and 9B show features of the Lateral Pinch Exerciser 90, which is an insert used in combination with the MUESS Basic Unit 10, that facilitates flexion of the metacarpophalangeal and interphalangeal joints of the thumb. Lateral Pinch Exerciser 90 may optionally include a clicker 92 to provide positive feedback of the desired exercise.

Common to the modular attachments, including the Web Space Widener 100, the Incremental Web Spacers 110, and the Graphomotor Tool Holder 120, are the following characteristics:

- Attaches directly to the Web Spacer Strap 20 of the MUESS Basic Unit 10.
- Maintains or widens web space between thumb and index finger.
- Initial size, and ensuing gradations, are determined by clinical reasoning of orthotist and/or therapist.

FIGS. 10A-D show features of the Web Space Widener 100 that provides tone inhibiting compression to mid-palm. The Web Space Widener 100 is preferably made from moldable silicone or other suitable material to form a firm, but flexible and comfortable projection, particularly as it passes over the web space. It narrows and thins as it curves away from the skin, passing over the web space between thumb and index finger, and places pressure on soft tissue only. Web Space Widener 100 ends at dorsal surface between metacarpals of index finger and thumb. The width may be increased or decreased as needed to accommodate change in passive range between thumb and index finger, as determined by orthotist and/or therapist. Web Space Widener 90 may be placed over Dynamic Wrap-Around 50 if an increase in stability in static position of hand, wrist, and forearm is needed.

Figure 11A:
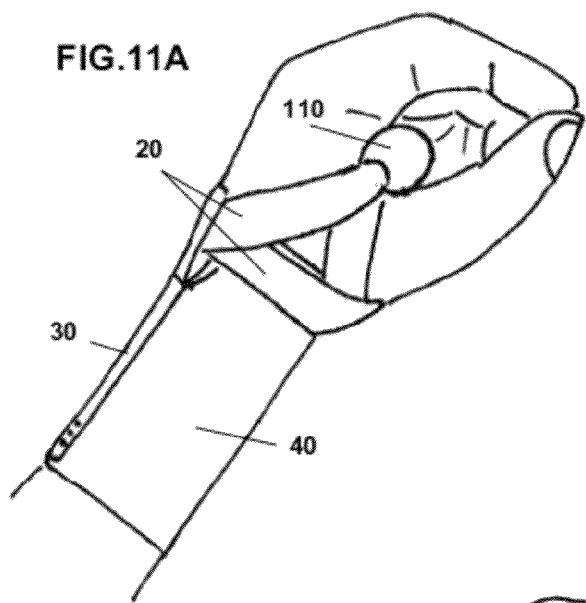
FIGS. 11A-C illustrate incremental web spacer elements of varying shapes and sizes for use in the MUESS.
Figure 11B:
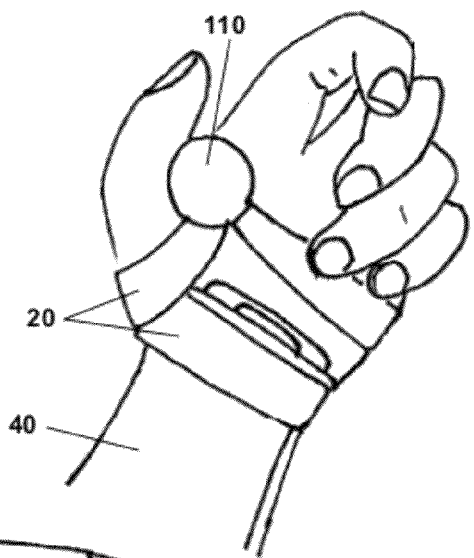
Figure 11C:
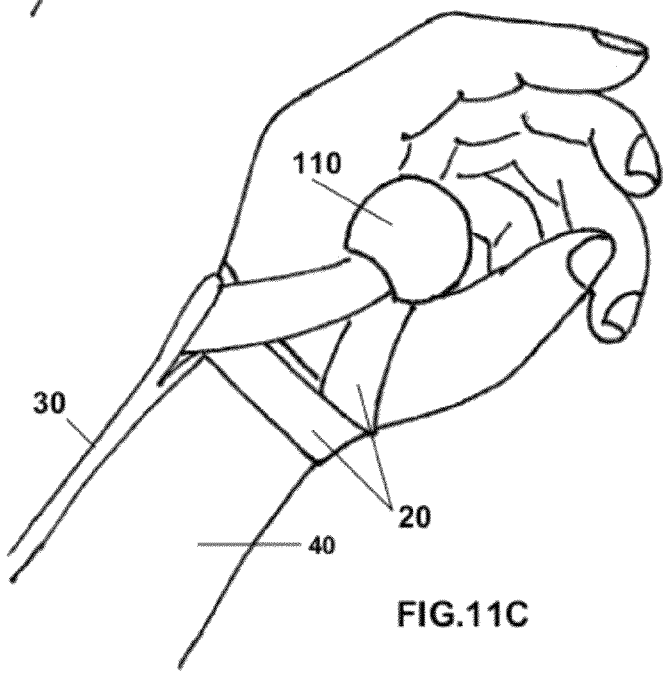

FIGS. 11A-C show features of Incremental Web Spacers 110 that facilitate metacarpophalangeal and interphalangeal joint flexion. Varying sizes and shapes gradually increase passive and or active range of motion of web space, as recommended by an orthotist or therapist. Graphomotor Tool Holder 120 as shown in FIGS. 12A-D facilitates a functional grasp for graphomotor activities.

Figure 13A:
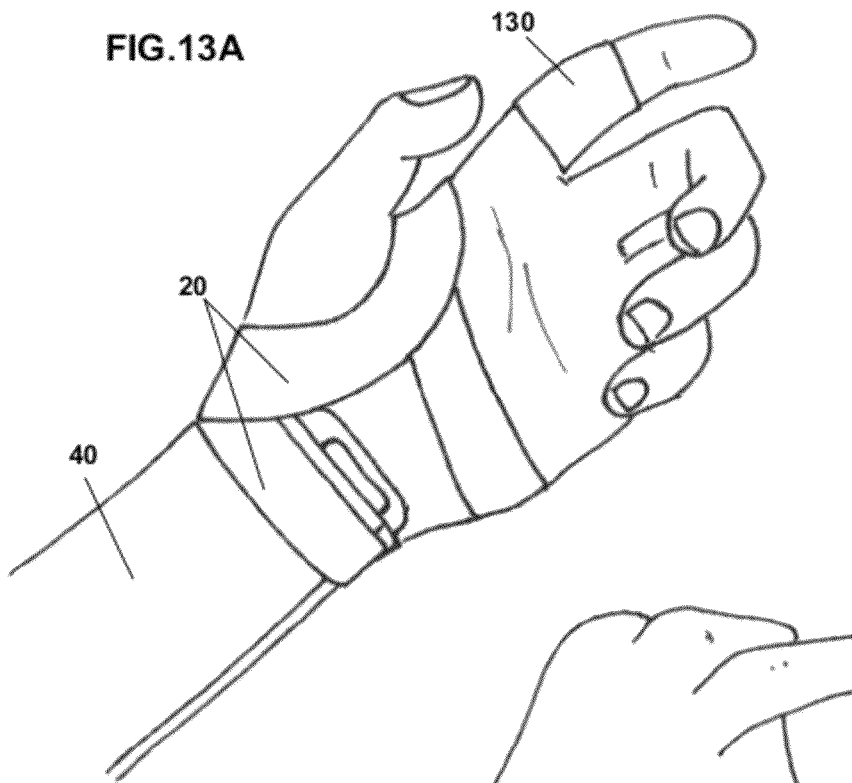
FIGS. 13A and 13B illustrate finger isolator elements for use in the MUESS.
Figure 13B:
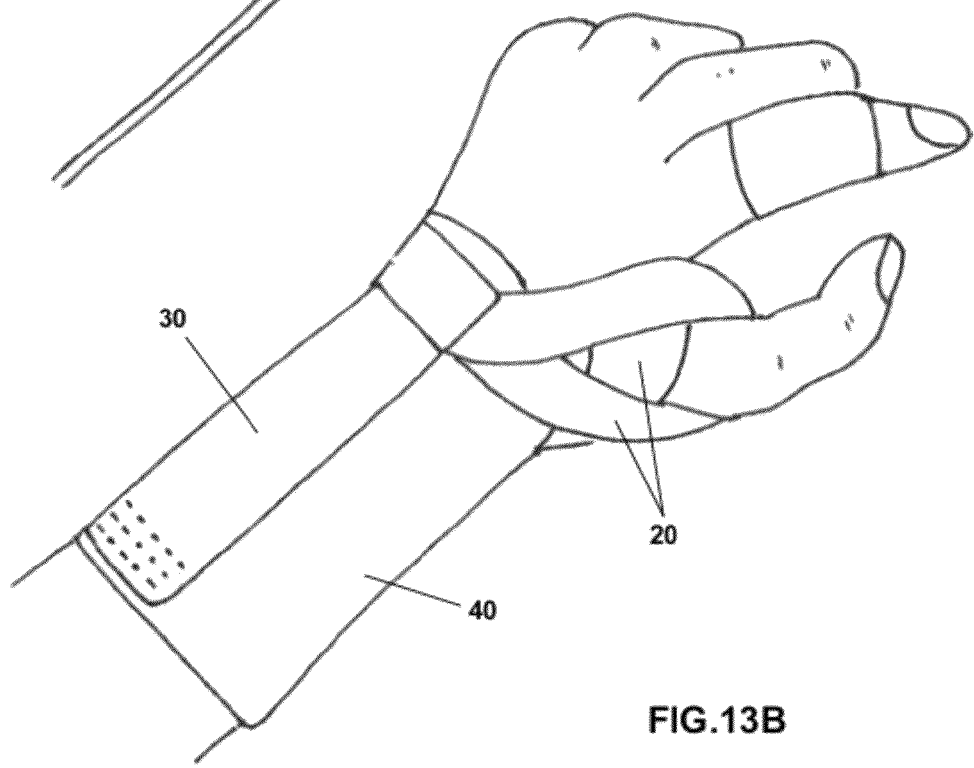
Figure 16D:
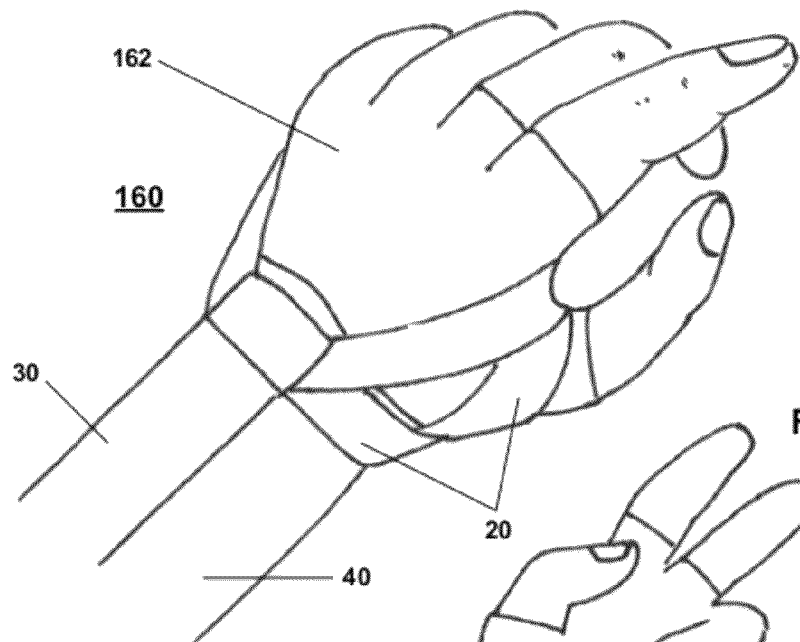
FIGS. 16A-D illustrate a radial/ulnar finger positioner element for use in the MUESS.
Figure 16A:
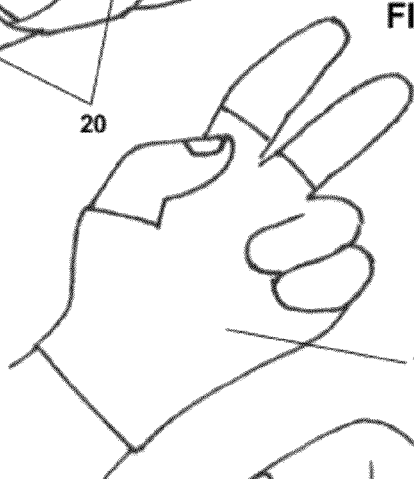
Figure 16B:
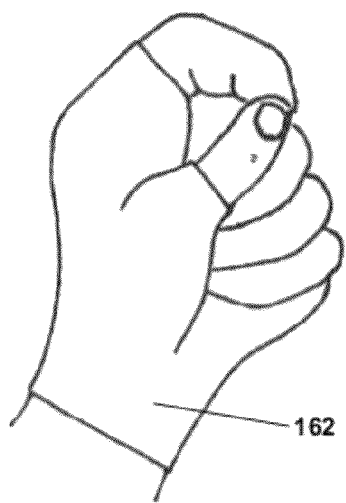
Figure 16C:
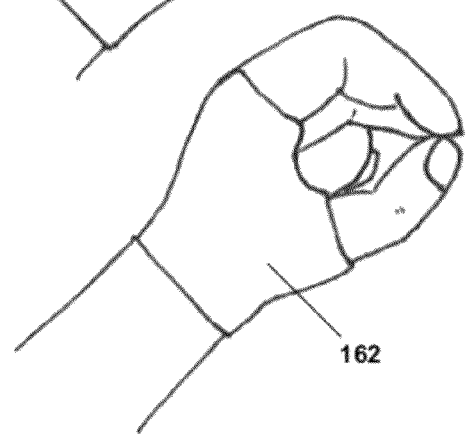

FIGS. 13A and 13B show features of Finger Isolators 130, which are individual finger cuffs used in conjunction with a Radial/Ulnar Finger Positioner 160 to assist in finger isolation by facilitating extension in the metacarpophalangeal, distal interphalangeal, and proximal interphalangeal joints of the finger(s). They can be used in combination with Lateral Pinch Exerciser 90, Ulnar/Radial Finger Positioner 160, or MUESS Basic Unit 10 when support needed for neutral hand position is minimal. A small strap can be used to connect Finger Isolator 130 with MUESS Basic Unit 10 when support is needed for extension at metacarpophalangeal joint(s).

FIGS. 14A and 14B show features of Hand/Wrist/Forearm Rotator 140, which is a modular attachment comprised of a long rotator strap 142 with a pocket 144 at distal end in which Web Spacer Strap 20 is encased. Hook and loop fastener 146 at proximal end of rotator strap 142 secures Hand/Wrist/Forearm Rotator 140 to upper arm just above elbow. Hand/Wrist/Forearm Rotator 140 facilitates supination of hand, wrist, and forearm away from nonfunctional position of pronation. Improvement of hand, wrist, and forearm into more functional position is facilitated by rotator strap 140. Pocket 144 of the Wrist/Forearm Rotator 140, is centered over the carpal bones on radial side of the wrist, over and just above, the styloid process of the radius. With the directional pull of the rotator strap 142, originating at the ulnar side of the carpal bones of the pronated hand, wrist, and forearm, varying degrees of supination are achieved, dependent on the tension the rotator strap exerts. Change of tension is obtained by lengthening or shortening rotator strap 142, respectively, with the degree of tension recommended by orthotist and/or therapist. With the elbow flexed to approximately 90 degrees, the Web Spacer Strap 20 of the Wrist/Forearm Rotator 140 is donned as it is with MUESS Basic Unit 10. The rotator strap 142 is then passed clockwise, over the distal volar surface of the forearm, making the first wrap around the mid-forearm, coming from the medial side before crossing over the elbow joint, before making the second wrap around above the elbow as the end of the rotator strap 140 forms a cuff on the upper arm and attaches to itself with hook and loop fastener 146.

FIGS. 15A-D show features of Weight Bearing Wrap 150, which is a modular insert used in combination with the MUESS Basic Unit 10, to inhibit the grasping reflex of a fisted hand. Weight Bearing Wrap 150 is constructed by laminating a center layer of flexible, coiled plastic between top and bottom layers of textured, non-slip material. The user's fingers are wrapped by a therapist around the top surface of the cylindrical shaped coil. A fisted hand of a child is passively positioned on a supporting surface, with slight pressure applied by therapist at wrist on dorsal surface as hand is slowly pulled back. With traction from the textured, non-slip material, both against volar surface of hand and supporting surface, the flexed fingers of the closed hand are passively drawn into extension, thereby facilitating full weight bearing on a fully extended hand.

FIGS. 16A-D show features of Radial/Ulnar Finger Positioner 160, which is a modular attachment in the form of a glove used to isolate the thumb, index and middle fingers, and thus increase their mobility. It is constructed from a snuggly fitting glove 162 which provides somatosensory input. The fabric of the glove is made from a material that is comfortable, breathable, with little stretch such as cotton. The glove may be sewn between the ring and little finger for tripod grasp facilitation. The glove may be sewn between the ring, little, and middle fingers for pinch grasp facilitation. For example, hook and loop fasteners on the pads of volar surfaces of distal phalanges of little and ring fingers may attach to upper segment of Web Spacer Strap 20 on volar surface of hand to stabilize the two ulnar fingers, respectively, and to allow mobility of the two radial fingers, thereby facilitating potential for tripod grasp with the thumb. Hook and loop fasteners on the pads of volar surfaces of distal phalanges of little, ring, and middle fingers may attach to an upper segment of Web Spacer Strap 20 on volar surface of the hand to stabilize the three ulnar fingers respectively, allowing mobility of one radial finger, thereby facilitating potential for a pincer grasp with the thumb. Radial/Ulnar Finger Positioner 160 may be used in combination with Lateral Pinch Exerciser 90 to stabilize hand in position of approximately 10 to 20 degrees of wrist extension, thereby allowing increased mobility of the thumb at metacarpophalangeal and interphalangeal joints.

FIGS. 17A and 17B show features of Resting Hand Support 170, which is a modular insert used in combination with the MUESS Basic Unit 10. It passively positions hand for rest, and maintains a present passive range of motion, while preventing deformities from occurring and/or worsening.

CONCLUSION

A system and method has been shown in the above embodiments for the effective implementation of a Modular Upper Extremity Support System. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:

1. A modular upper extremity support system (MUESS) basic unit comprising:
   a forearm cuff adapted to surround an individual user's forearm;
   a wrist extensor strap adapted to be attached to the forearm cuff along a dorsal side of the user's forearm; and
   a web spacer strap comprising a first loop at a first end of the web spacer strap that is adapted to wrap around a user's thumb proximal to a metacarpophalangeal joint before crossing a volar surface of the user's hand and a second loop at a second end of the web spacer strap that is adapted to wrap around the user's thumb proximal to the metacarpophalangeal joint after crossing a dorsal surface of the user's hand, where the web spacer strap does not cover the metacarpophalangeal or interphalangeal thumb joints;
   wherein the wrist extensor strap comprises a pocket at a distal end that captures and secures said web spacer strap.

2. The system of claim 1, wherein said forearm cuff further comprises at least one support pocket for holding an orthotic insert, said support pocket located on the inside of said forearm cuff and adapted to be adjacent to said user's skin along the volar side of said user's forearm.

3. The system of claim 2, wherein said at least one support pocket comprises a plurality of pockets of varying width.

4. The system of claim 2, further comprising an orthotic insert adapted to fit into said at least one support pocket, said orthotic insert selected from a group consisting of: a dynamic wrap-around, a mobile joint facilitator, a wrist/ulnar support, a toy/tool holder, a lateral pinch exerciser, a weight bearing wrap, and a resting hand support.

5. The system of claim 1, further comprising a modular attachment adapted to attach to said web spacer element, said modular attachment selected from a group consisting of: a web space widener, an incremental web spacer, and a graphomotor tool holder.

6. The system of claim 1, further comprising a modular attachment selected from a group consisting of: a finger isolator, a hand/wrist/forearm rotator, and a radial/ulnar finger positioner.

7. The system of claim 1, wherein said web spacer strap further comprises a sliding fastener that adjusts the circumference of said web spacer strap.

8. The system of claim 1, wherein said web spacer strap further comprises a hook and loop fastener to attach a portion of said web spacer strap directly to said forearm cuff.

9. The system of claim 1, wherein said wrist extensor strap is attached to said forearm cuff with a repositionable hook and loop fastener.

10. A method of treating hand dysfunction in an individual user, said method comprising the steps of:
wrapping a forearm cuff around a forearm of the user;
looping a first loop of a web spacer strap around the user's thumb below a metacarpophalangeal joint;
running said web spacer strap across a volar surface of the user's hand, around an ulnar side of the user's hand, and across a dorsal side of the user's hand, said web spacer strap passing through a pocket in a distal end of a wrist extensor strap;
looping a second loop of said web spacer strap around the user's thumb below the metacarpophalangeal joint;
and attaching said wrist extensor strap to the dorsal side of the forearm cuff.

11. The method of claim 10, wherein said forearm cuff further comprises at least one support pocket for holding an orthotic insert, said support pocket located on the inside of said forearm cuff and adapted to be adjacent to said user's skin along the volar side of said user's forearm.

12. The method of claim 11, wherein said at least one support pocket comprises a plurality of pockets of varying width.

13. The method of claim 11, further comprising the step of inserting an orthotic insert into said at least one support pocket, said orthotic insert selected from a group consisting of: a dynamic wrap-around, a mobile joint facilitator, a wrist/ulnar support, a toy/tool holder, a lateral pinch exerciser, a weight bearing wrap, and a resting hand support.

14. The method of claim 10, further comprising the step of attaching a modular attachment to said web spacer element, said modular attachment selected from a group consisting of: a web space widener, an incremental web spacer, and a graphomotor tool holder.

15. The method of claim 10, further comprising the step of attaching a modular attachment selected from a group consisting of: a finger isolator, a hand/wrist/forearm rotator, and a radial/ulnar finger positioner.

16. The method of claim 10, further comprising the step of adjusting the circumference of said web spacer strap by sliding a fastener.

17. The method of claim 10, further comprising the step of attaching a portion of said web spacer strap directly to said forearm cuff with a hook and loop fastener.

18. The method of claim 10, further comprising the step of adjusting the position of said wrist extensor strap in the proximal or distal direction according to the medical needs of the user.

19. A modular upper extremity support system (MUESS) comprising:
a forearm cuff adapted to surround an individual user's forearm, said forearm cuff comprises a plurality of support pockets of varying width located on an inside of said forearm cuff and adapted to be adjacent to said user's skin along a volar side of said user's forearm;
a wrist extensor strap adapted to be attached to the forearm cuff along a dorsal side of the user's forearm;
a web spacer strap comprising a first loop at a first end of the web spacer strap that wraps around a user's thumb proximal to a metacarpophalangeal joint before crossing a volar surface of the user's hand and a second loop at a second end of the web spacer strap that wraps around the user's thumb proximal to the metacarpophalangeal joint after crossing a dorsal surface of the user's hand; wherein said wrist extensor strap comprises a pocket at a distal end that captures and secures said web spacer strap; and
a modular element selected from a group consisting of: a dynamic wrap-around, a mobile joint facilitator, a wrist/ulnar support, a toy/tool holder, a lateral pinch exerciser, a web space widener, an incremental web spacer, a graphomotor tool holder, a finger isolator, a hand/wrist/forearm rotator, a weight bearing wrap, a radial/ulnar finger positioner, and a resting hand support.

* * * * *